United States Patent [19]
Turriff et al.

[11] Patent Number: 5,505,098
[45] Date of Patent: Apr. 9, 1996

[54] SOIL SAMPLE CONTAINMENT CARTRIDGE WITH DETACHABLE HANDLE

[75] Inventors: David E. Turriff; Lloyd E. Jacobs, both of Green Bay, Wis.

[73] Assignee: En Chem, Inc., Green Bay, Wis.

[21] Appl. No.: 391,117

[22] Filed: Feb. 21, 1995

Related U.S. Application Data

[60] Division of Ser. No. 241,445, May 11, 1994, abandoned, which is a continuation-in-part of Ser. No. 915,309, Jul. 20, 1992, Pat. No. 5,343,771.

[51] Int. Cl.[6] .................................................. G01N 1/08
[52] U.S. Cl. ............................. 73/864.44; 175/20
[58] Field of Search ........................ 73/864.44, 864.45, 73/864.91, 864.41; 172/21, 22; 175/20, 58, 244, 321, 249, 246, 309, 226

[56] References Cited

U.S. PATENT DOCUMENTS

| | | | |
|---|---|---|---|
| D. 269,844 | 7/1983 | Hackerson | D8/7 |
| 1,109,446 | 9/1914 | Melberg . | |
| 1,162,901 | 9/1915 | Cantey . | |
| 2,643,858 | 6/1953 | Hardman | 255/1.4 |
| 2,664,269 | 12/1953 | Knight et al. | 255/1 |
| 3,146,838 | 9/1964 | Tijmann et al. | 175/405 |
| 3,176,053 | 3/1965 | DiStasio | 264/31 |
| 3,224,512 | 12/1965 | Alexander | 173/19 |
| 3,326,049 | 6/1967 | Eley | 73/429 |
| 3,444,938 | 5/1969 | Ballmann | 175/173 |
| 3,497,018 | 2/1970 | Shulz et al. | 175/6 |
| 3,707,197 | 12/1972 | Walesch et al. | 175/20 |
| 3,986,555 | 10/1976 | Robertson | 166/246 |
| 4,014,393 | 3/1977 | Henzel, Jr. | 175/58 |
| 4,096,749 | 6/1978 | Stewart | 73/425.2 |
| 4,116,247 | 9/1978 | Zanasi | 141/392 |
| 4,336,849 | 6/1982 | Hug | 175/246 |
| 4,549,612 | 10/1985 | Cushing | 175/20 |
| 4,653,336 | 3/1987 | Vollweiler | 73/864.44 |
| 4,729,437 | 3/1988 | Zapico | 175/20 |
| 4,733,469 | 3/1988 | Haglöf | 30/130 |
| 4,819,735 | 4/1989 | Puckett | 172/22 |
| 4,840,517 | 6/1989 | Bullivant | 405/241 |
| 4,848,484 | 7/1989 | Clements | 175/20 |
| 4,860,599 | 8/1989 | Griffis | 73/864.45 |
| 4,887,413 | 12/1989 | Tuckey, Jr. | 53/520 |
| 4,888,999 | 12/1989 | Kozak | 73/864.65 |
| 4,989,678 | 2/1991 | Thompson | 175/20 |
| 5,005,433 | 4/1991 | Patton | 73/864.44 |
| 5,186,263 | 2/1993 | Kejr | 175/20 |
| 5,245,878 | 9/1993 | Underwood | 73/864.45 |

*Primary Examiner*—Hezron E. Williams
*Assistant Examiner*—Nashmiya Ashraf
*Attorney, Agent, or Firm*—Jansson & Shupe, Ltd.

[57] ABSTRACT

Disclosed is a tool-like cartridge for preserving a soil sample which may be contaminated with a volatile organic compound (VOC). The cartridge includes a barrel and a plug in the barrel for sealing the barrel proximal end during and after sampling and for later expelling the soil sample from such barrel. A threaded portion is on the barrel for attaching a handle and such portion has an opening through it. From the moment of sample extraction until later sample expulsion for analysis, the plug and its resilient seal member substantially prevent vaporized VOC from escaping from the cartridge. A new method for obtaining a soil sample for analysis is also disclosed.

6 Claims, 8 Drawing Sheets

SOIL SAMPLE CONTAINMENT CARTRIDGE WITH DETACHABLE HANDLE

RELATED APPLICATIONS

This application is a division of application Ser. No. 08/241,445 filed May 11, 1994, now abandoned, which is a continuation-in-part of application Ser. No. 07/915,309 filed Jul. 20, 1992, now U.S. Pat. No. 5,343,771 issued on Sep. 6, 1994.

FIELD OF THE INVENTION

This invention relates generally to devices used for testing and, more particularly, to devices used for soil testing.

BACKGROUND OF THE INVENTION

Soil sampling tools and devices are used for a variety of purposes, e.g., to obtain samples for soil moisture content or to sample a volatile organic compound (VOC) which may have permeated the soil. And soil cores are removed for other reasons unrelated to VOC analysis. Examples of soil coring and sampling tools are shown in U.S. Pat. Nos. 3,326,049 (Eley); 3,444,938 (Ballman); 3,497,018 (Schultz et al.) and 4,989,678 (Thompson).

The device shown in the Eley patent has a barrel with air vent and a shaft threaded to the barrel. The shaft is graduated so that when turned, the soil sample is ejected in increments. The kit shown in the Thompson patent includes a sampling device and a sample containment device, both of which are used for analyzing a soil sample containing a VOC.

It is common knowledge that tanks for storing liquids may, over time, develop a leak. If the tank is above ground, the leak is usually observed rather soon after its onset and not much damage results. On the other hand, there is an already-substantial and growing awareness that certain types of liquid storage tanks placed underground have a greater-than-normal propensity to deteriorate and leak. Such types include tanks made of common sheet steel from which protective coatings have either been eaten away or were non-existent. And a substantial factor contributing to the risk of tank leakage is that with an underground tank, leakage is not visible. Usually, such leakage can only be detected by excavation and testing.

And the risks are enormous. Undetected leaks of underground storage tanks can and do contaminate soil and potable water supplies, the latter by polluting underground aquifers from which a great deal of drinking water is drawn. Recent legislation recognizes risks presented by leaking underground storage tanks and provides for remediation of damage caused by such leaks. Because of the number of gasoline service stations and private fuel and solvent storage tanks, leakage of petroleum distillates and hydrocarbons is a particularly significant problem.

Good remediation requires that personnel be able to accurately determine the nature and extent of the leak. Such determination depends in large part upon the availability of high quality test instruments and the ability to preserve the integrity of a soil sample (and, particularly, to prevent evaporation of VOCs therein) once the sample is taken. The efforts of earlier workers in this regard have not been entirely satisfactory.

For example, the Thompson patent emphasizes speed of transfer of a soil sample from a sampling tool to a containment device to minimize loss of VOC. This is a less-than-fully-satisfactory solution to retention of sample integrity, especially if the leaky tank was installed at a site distant from the analyst's laboratory. Other known prior art patents show soil sampling tools having handles which are not easily removed. And if removable, there is no good way to seal that end of the barrel from which the handle is removed. To put it another way, earlier known sampling tools fail to offer optimum solutions for preserving VOCs in soil samples and for reducing the substantial storage space required to transport what may be dozens of tools to and from a site.

OBJECTS OF THE INVENTION

It is an object of the invention to provide a soil sample containment cartridge overcoming some of the problems and shortcomings of the prior art.

Another object of the invention is to provide a soil sample containment cartridge which preserves the integrity of the VOC in a soil sample.

Yet another object of the invention is to provide a soil sample containment cartridge which avoids sample contamination.

Another object of the invention is to provide a soil sample containment cartridge which saves substantial space when transporting samples from a possibly-contaminated site to a laboratory. How these and other objects are accomplished will become apparent from the following descriptions and the drawing.

SUMMARY OF THE INVENTION

Aspects of the invention involve a method for obtaining a soil sample using a unique tool-like soil sample containment cartridge. Such method includes the steps of providing a generally-cylindrical cartridge having an open distal end and a proximal end sealed by a removable plug. A removable handle is attached to the cartridge and the cartridge then used to "core out" and extract a soil sample.

Following sample extraction, the "mouth portion" at the distal end is closed, preferably by applying a cap to such mouth portion. For optimum sealing, the applying step includes compressing a resilient seal between the cap and the mouth portion. And the handle is detached but end closure and handle detachment may be in either order. Using such method, the soil sample and any VOC therewith is quickly "captured" in the cartridge for preservation, transport and later analysis.

In other aspects of the method, the handle detaching step is followed by the steps of transporting the cartridge for analysis and moving the plug along the cartridge barrel toward its mouth portion to expel the soil sample from the cartridge. To move the plug, a rod-like implement is provided for applying force to the plug. The implement is coupled to the plug and the plug and soil sample pushed out.

Structural aspects of the invention involve a tool-like cartridge for preserving a core-like soil sample after such sample has been removed from a site possibly contaminated with VOC. The cartridge has a barrel, a plug in the barrel for expelling a soil sample therefrom and an attachment portion on the barrel and having an opening therethrough. The plug has a stud extending through the opening and a seal between the plug and the attachment portion prevents VOC from escaping through such opening. The plug is secured by a nut threaded to the stud. When so sealed, the cartridge is suitable for preserving a soil sample containing a volatile organic compound.

More specifically, the plug has an imperforate face plate and a sealing member is interposed between the face plate and the attachment portion for sealing the opening. Preferably, such member is a resilient seal such as an O-ring. And if the attachment portion is threaded or otherwise configured for easy handle attachment and detachment, there is a cover for protecting such portion.

At its end opposite the attachment portion, the cartridge has a mouth portion and a cap sealing the mouth portion. Such cap prevents VOC vapors from escaping from the mouth end of the cartridge after sample extraction and before the sample is transported to and analyzed in a laboratory.

Other aspects of the invention make it easy to expel the well-preserved soil sample from the cartridge after such cartridge has been transported to a laboratory. Quick, easy expulsion of the sample to a containment vial for analysis is important to preserve any VOC present in such sample.

In a preferred procedure, one (or, more typically, several) cartridges are supplied to the user, each having its plug stud extended through the opening of its attachment portion and held there by a nut. When the stud is so positioned, the sealing member is compressed against the attachment portion and the proximal end of the cartridge is thereby sealed. A handle is also supplied.

To collect a possibly-contaminated soil sample, the handle is attached to the cartridge and the barrel of the assembled tool forced into the earth and then withdrawn with a "core" of soil inside. A cap is promptly placed on the mouth portion, the handle is removed and the sample, now completely sealed in the cartridge, is ready to be transported to a laboratory. If the handle is attached to the cartridge by threads, it is desirable to protect the cartridge threads with a cover after removing the handle but before cartridge transportation.

The stud includes an interior cavity having a threaded cavity wall. When the lab analyst is ready to expel the sample from the barrel, the nut is removed and a rod-like implement is attached to the stud for pushing the plug toward the mouth portion and expelling the sample.

Other details of the invention are set forth in the following detailed description and in the drawing.

DETAILED DESCRIPTIONS OF PREFERRED EMBODIMENTS

The improved soil sampling tool 10 is particularly useful in collecting soil samples 11 permeated with a VOC. As described below, the tool 10 has new features facilitating sample preservation, storage, transportation and identification. Such features will be welcomed by those having responsibilities for leak-site analysis and remediation.

Figure 1:
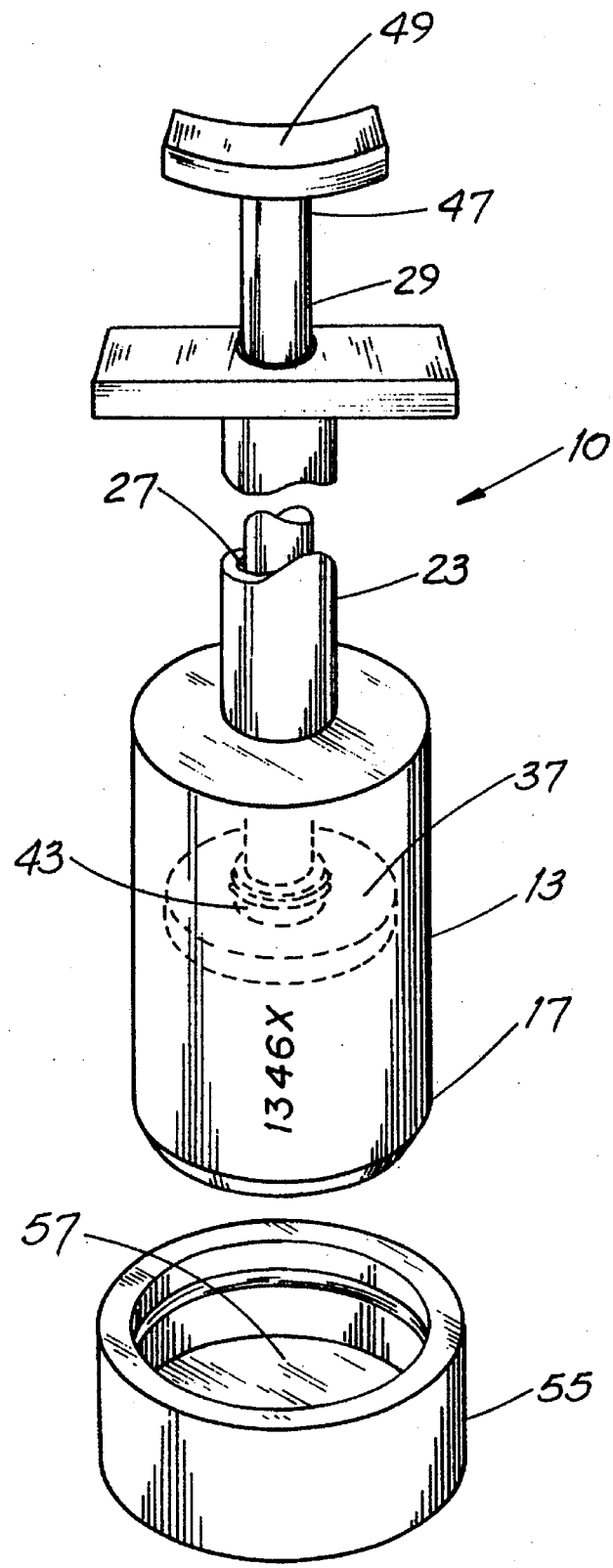
FIG. 1 is a perspective view of an embodiment of the improved tool with parts broken away and other parts shown in phantom outline.
Figure 2:
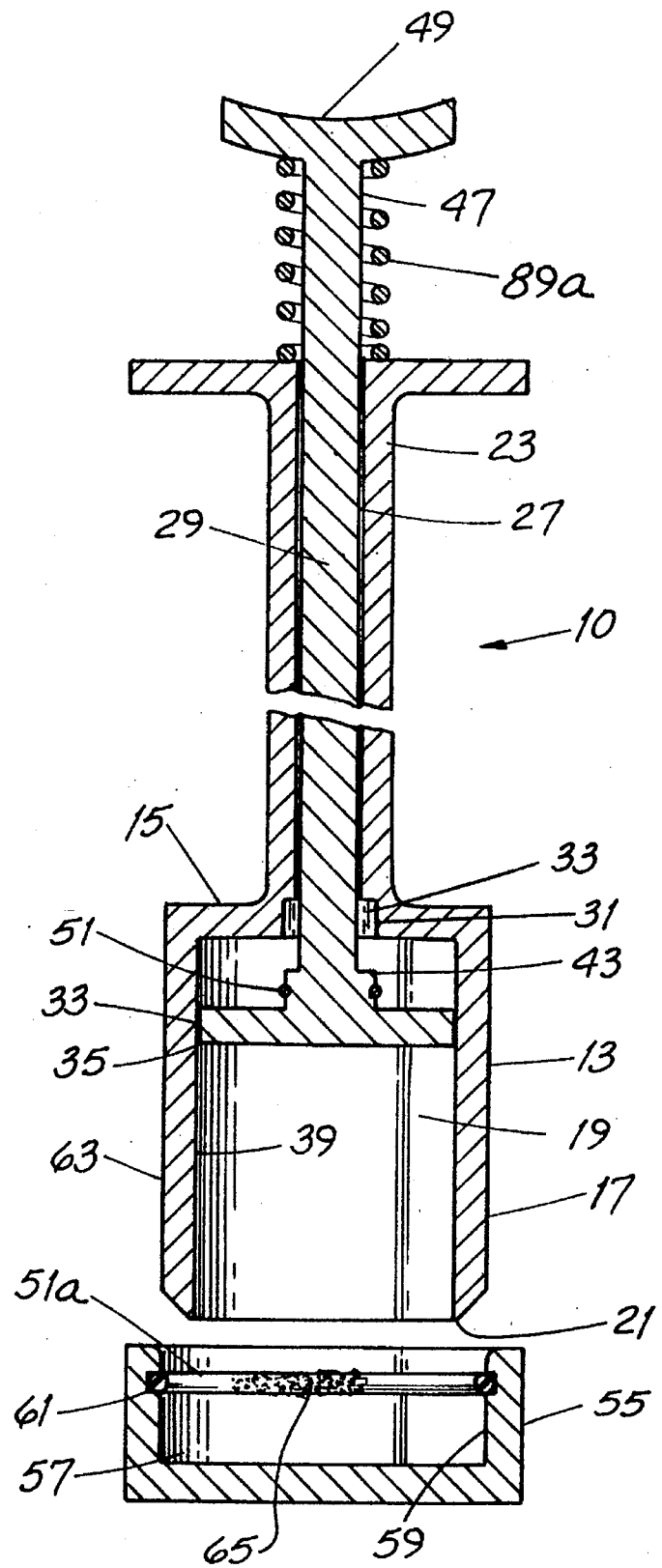
FIG. 2 is, generally, a cross-sectional view of the tool of FIG. 1 taken along a viewing plane coincident with the longitudinal tool axis, with parts broken away and other parts shown in full representation.

Referring first to FIGS. 1 and 2, the improved sampling tool 10 includes a hollow, generally cylindrical barrel 13 having an end wall 15 and a mouth portion 17. The interior region 19 of the barrel 13 is of generally uniform diameter along its length and has a volumetric capacity of 25–30 grams, for example. The edge 21 of the mouth portion 17 is bevelled inward, resulting in a relatively sharp soil-cutting "blade."

Figure 4:
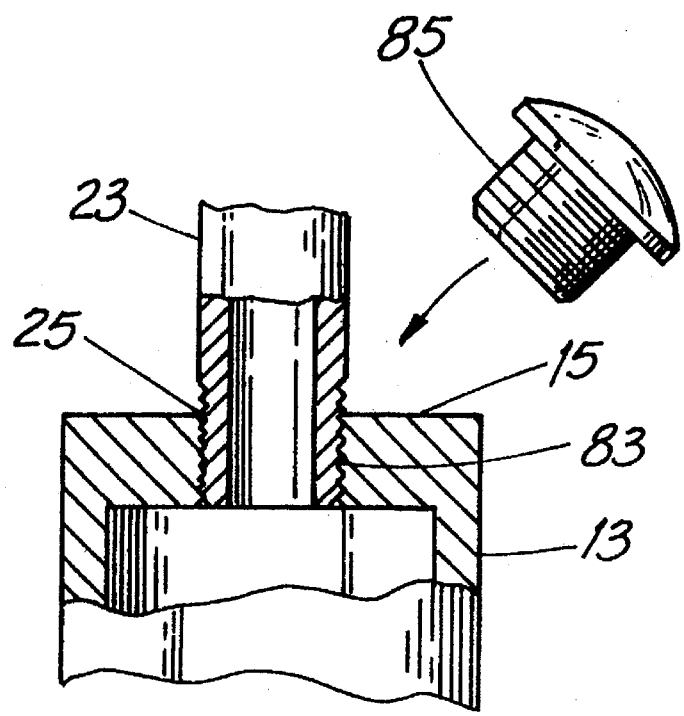
FIG. 4 is a cross-sectional side elevation view, with parts broken away, showing a variation of a portion of the tool of FIG. 1.

An elongate, tube-like handle 23 is concentrically attached to the barrel end wall 15. In a preferred embodiment, the handle 23 is separably attached to the end wall 15 (by a threaded connection 25, for example as shown in FIG. 4) so that the handle 23 and barrel 13 can be readily attached to and detached from one another for purposes described below. The T-shaped handle shown in FIGS. 1 and 2 is preferred in situations where soil samples 11 are expected to be taken from dense, relatively hard soils such as clay soils. The T-shaped handle 23 affords an opportunity to apply a substantial insertion force to the tool 10.

The handle 23 has a passage 27 extending along its length for receiving a rod-like ejector 29 and the handle 23, passage 27 and ejector 29 are preferably circular in cross-sectional shape. The diameters of the passage 27 and the ejector 29 are cooperatively selected to provide slight clearance therebetween so that the ejector 29 may move freely within the passage 27.

As best seen in FIG. 2, the barrel 13 has an end aperture 31 and the ejector 29 and aperture 31 define an air exhaustion clearance 33 between them. Since there is just enough space between the rim 35 of the plunger 37 and the interior wall 39 of the barrel 13 to permit relatively free sliding plunger movement, such clearance 33 permits air to escape along the passage 27 as the tool 10 is urged into soil and the plunger 37 is thereby driven toward the end wall 15.

Figure 3:
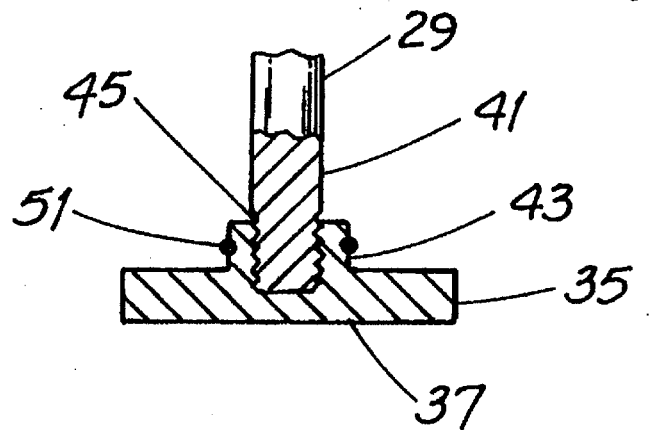
FIG. 3 is a side elevation view, partly in cross-section, of the tool plunger and ejector.
Figure 5:
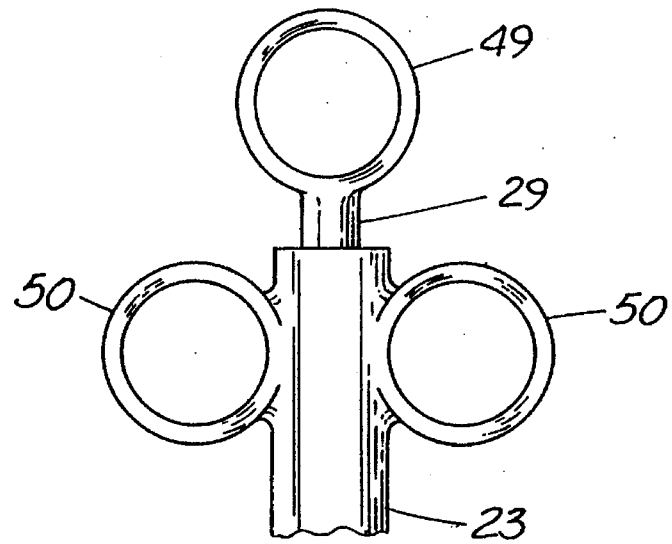
FIG. 5 is a side elevation view, with parts broken away, showing a variation of another portion of the tool of FIG. 1.

Referring additionally to FIG. 3, a disc-like plunger 37 is mounted to the distal end 41 of the ejector 29 and has a boss 43 extending a short distance from the plunger 37. For reasons described below, the ejector 29 and plunger 37 are preferably readily attachable to and detachable from one other. In the illustrated exemplary embodiment, the boss 43 has a threaded pocket 45 and the ejector distal end 41 is similarly threaded for attachment to the boss 43. At its proximal end 47, the ejector 29 includes a thumb engagement member 49 so that when the handle 23 and member 49 are grasped "hypodermic fashion," the member 49 may be depressed toward the handle 23 to eject a soil sample 11 from the barrel 13. And as shown in FIG. 5, the thumb engagement member 49 may be ring-like in shape and a handle 23 with side rings 50 may be provided instead of the T-shaped handle 23 shown in FIGS. 1 and 2.

Since such samples 11 are usually transported to a laboratory for analysis, it is highly preferred that VOC vapors be prevented from escaping from the sample 11 and from the tool 10 through the aperture 31. Diminution of the amount of vapor and VOC present in the sample 11 will "skew" the test results and may cause the level of soil contamination to appear less than it actually is. Accordingly, the plunger boss 43 seals the aperture 31 when the plunger 37 is closely adjacent to or in contact with the barrel end wall 15. Sealing is by a resilient O-ring 51 seated in a circumferential groove in the outer surface of the boss 43.

Figure 9:
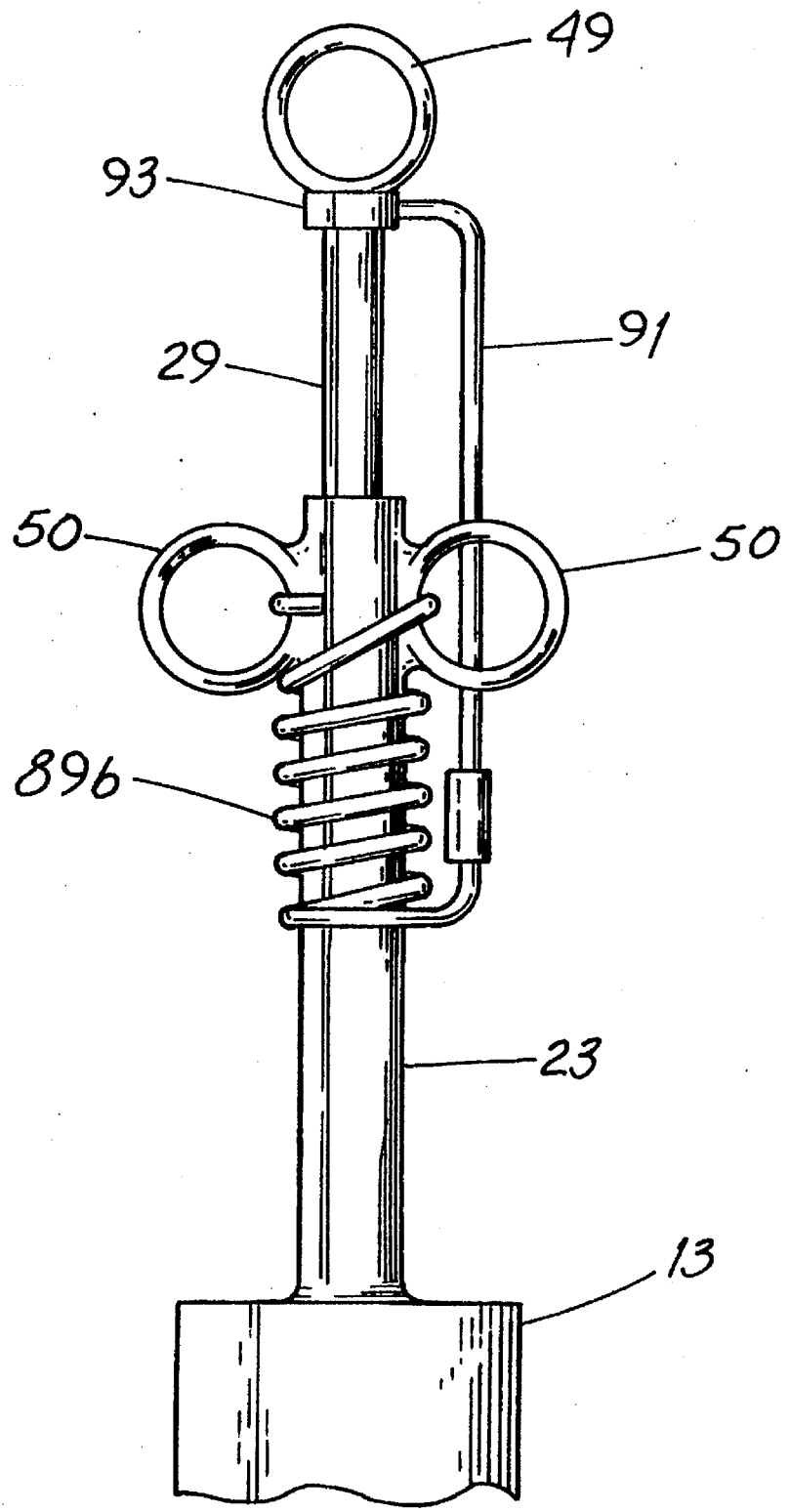
FIG. 9 is a side elevation view of a variation of the tool including a biasing spring.

It is highly preferred that the aperture 31 be sealed even as the tool barrel 13 starts penetrating into the soil. In the embodiments described above, the plunger 37 may be spaced away from the barrel end wall 15 when penetration starts, especially if the tool 10 is prior held with the barrel 13 downward. Referring to FIGS. 1 and 9, the plunger 37 is biased by a spring 89a or 89b to the sample-extracting position, i.e., that position at which the plunger 37 seals the aperture 31. In that way, VOC vapors are prevented from escaping through the aperture, especially at the onset of sample "cutting."

In the arrangement of FIG. 1, the compression spring 89a is interposed between the handle 23 and the thumb engagement member 49. In the arrangement of FIG. 9, the tension spring 89b is attached to and extends from the side rings 50 downward (as viewed in FIG. 9) along the handle 23. A coupler rod 91 extends between the lower end of the spring 89b and a collar 93 immediately below the member 49. In each instance, the spring 89a, 89b biases the ejector 29 and its plunger 37 upward to seal the aperture 31. The aperture 31 may be sealed by an O-ring 51 on the plunger boss 43 as described below.

Figure 10:
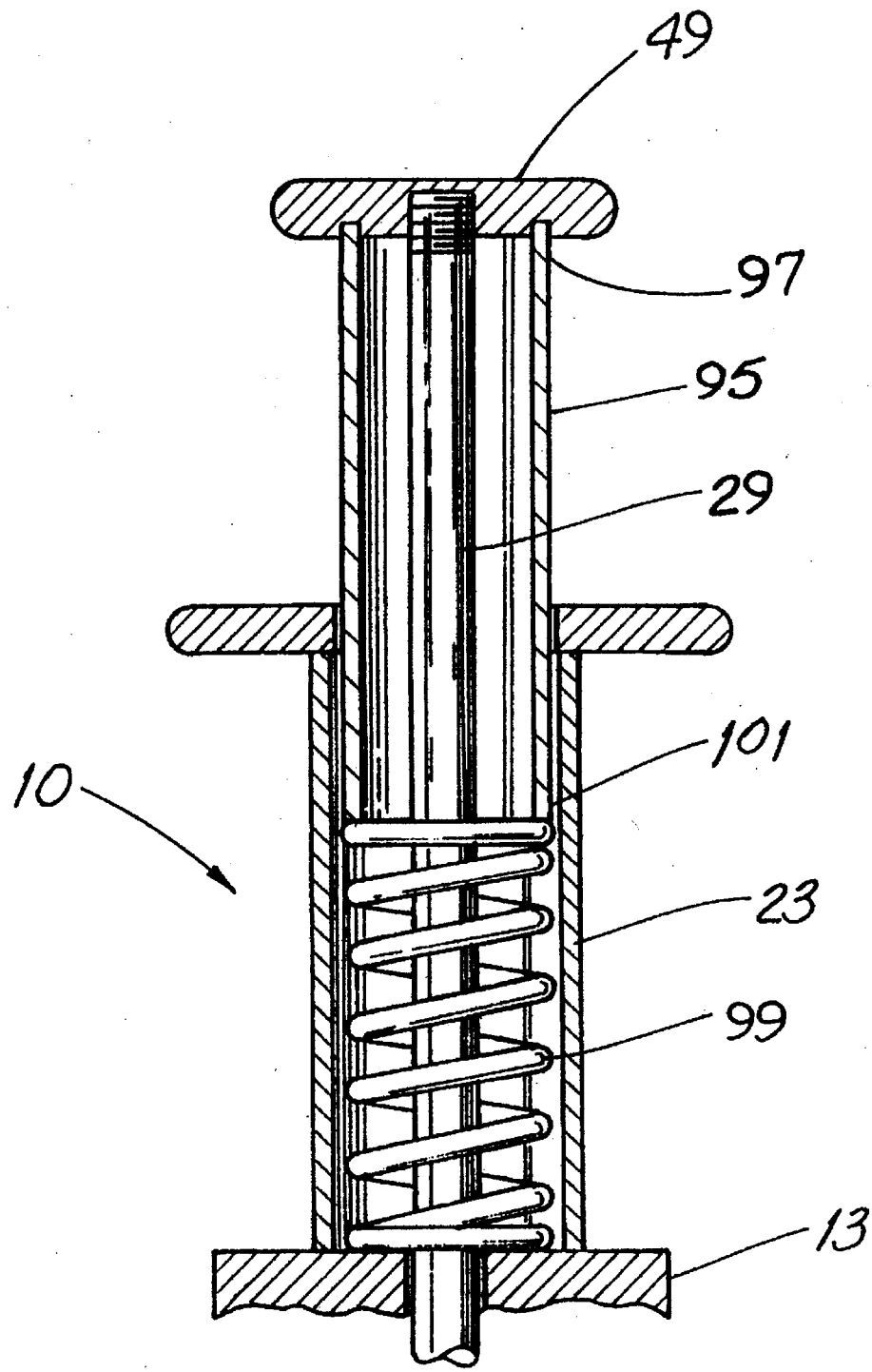
FIG. 10 is a side elevation view, partly in cross-section and with parts broken away, of another variation of the tool including a biasing spring.

In the arrangement of FIG. 10, the tool 10 includes a hollow tube 95 received telescope-fashion in the handle 23. The upper end 97 of the tube 95 is attached to a thumb engagement member 49 as is the ejector 29. A compression spring 99 is confined between the lower end 101 of the tube 95 and the top of the barrel 13. The spring 99 biases the tube 95, member 49 and ejector 29 upward in the absence of downward force on the member 49.

Figure 8:
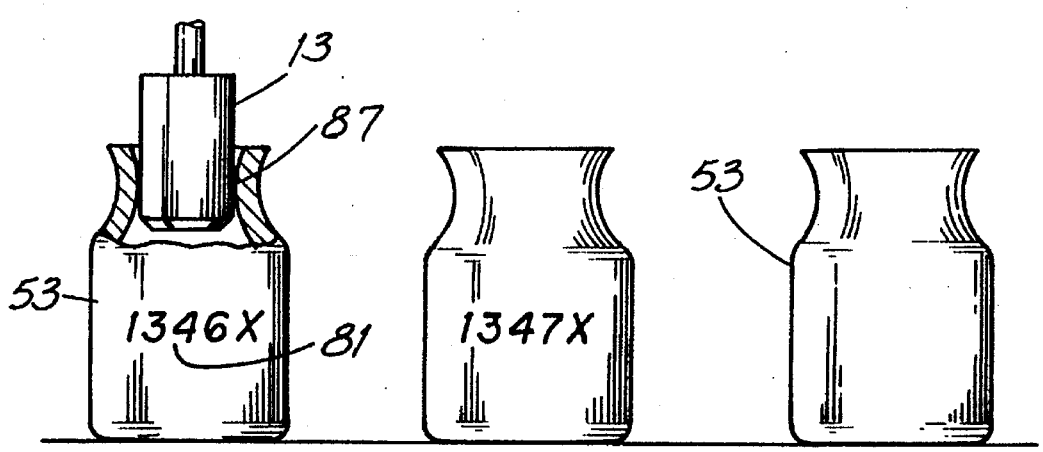
FIG. 8 illustrates how a soil sample is ejected into a vial for later sample analysis.

Referring further to FIGS. 1 and 2 and to FIG. 8, it is preferred that the barrel interior region 19 be completely sealed after a soil sample 11 is taken but before the sample 11 is ejected to a vial 53 for sample analysis. To that end, the improved tool 10 also includes a cup-like cap 55 which has an interior cavity 57 and a cavity wall 59. The cap cavity 57 has a cross-sectional shape generally conforming to that of the barrel 13 which, in the preferred embodiment, is cylindrical. A resilient O-ring 51a is seated in a circumferential groove 61 formed in the cavity wall 59. Such O-ring 51a helps assure a vapor-tight seal against the mouth portion 17 when the cap 55 is placed on such portion 17.

It should be understood that sealing the barrel interior region 19 can be accomplished in other ways. For example, the boss 43 and aperture 31 can be formed to permit very closely fitted, sliding clearance between them and thereby provide a relatively good vapor seal. The barrel outer wall 63 and the cap cavity wall 59 can be similarly formed. However, use of O-ring seals 51, 51a permits some "forgiveness" in certain manufacturing dimensional tolerances and should result in a reduced manufacturing cost.

As explained in the summary, when O-rings 51, 51a are used for sealing, some difficulty may be experienced in positioning the sealing "pieces" (the boss 43 or the cap 55) to a fully seated position if the pieces are not made to close tolerances. If needed, a seal lubricant 65 may be applied to the rings 51, 51a and nearby surfaces to help avoid such difficulty. However, care must be taken to avoid sample contamination by a petroleum-based product such as a lubricating oil. Therefore, a highly preferred lubricant 65 is powdered graphite.

Figure 6:
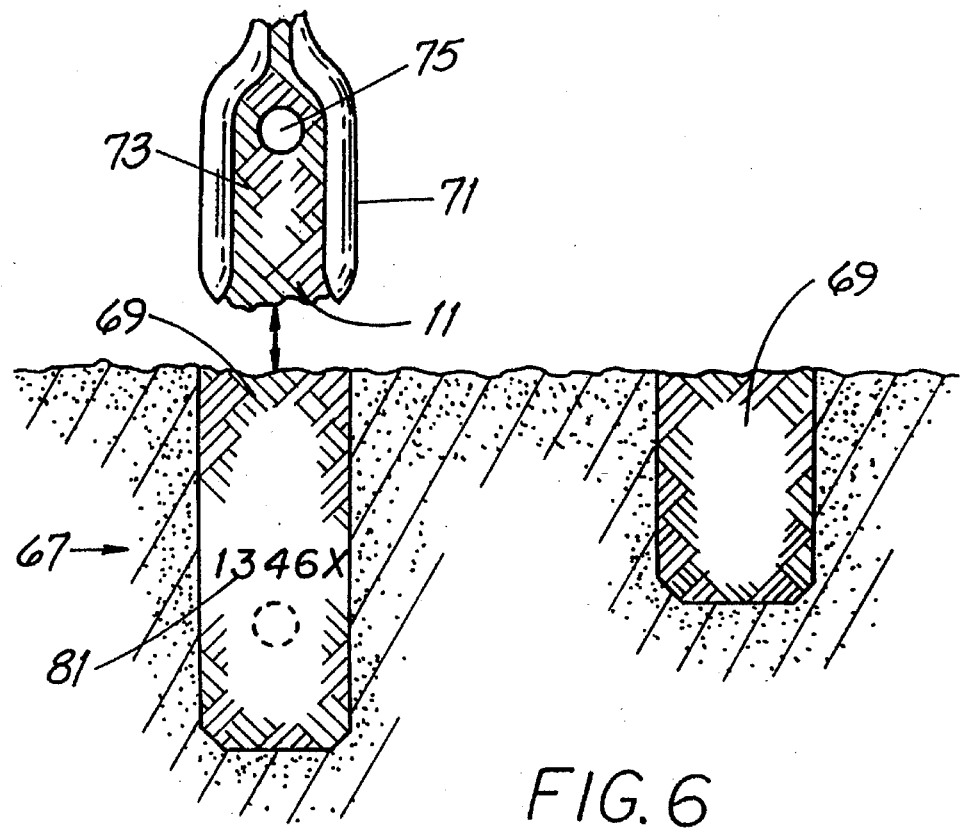
FIG. 6 is a representative cross-sectional side elevation view of a suspected leaky underground storage tank site which is to be analyzed using bored holes.

The following is an explanation of how and where soil samples 11 are taken and identified and how such samples 11 are handled in preparation for lab analysis. It is assumed that the site 67 of a suspected leaking underground storage tank has been identified and such site 67 is shown generally in FIGS. 6 and 7. As shown in FIG. 6, those involved in determining whether and to what extent contamination exists at the site 67 will bore holes 69 (to avoid sampling at the earth surface where VOC and vapors may be less concentrated) and use what is known as a split spoon device 71 (resembling a "plunge type" post hole digger) to extract relatively large "slugs" 73 of soil from various holes 69. Using the tool 10, a soil sample is taken from a location 75 (or perhaps two or more locations) on the slug 73. Each slug 73 is removed at a known depth and from a hole 69 have a known location. Both such informational items are recorded for "mapping" the site 67 with a field sketch.

Figure 7:
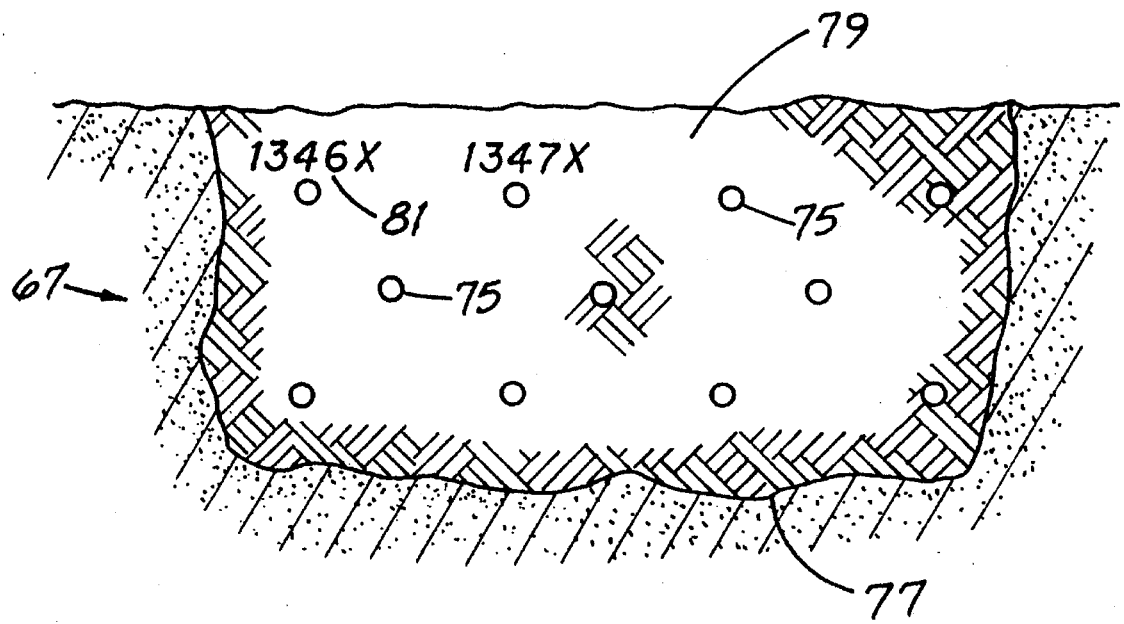
FIG. 7 is a representative cross-sectional side elevation view of a site like that of FIG. 6 which is being analyzed using a dug hole.

Referring to FIG. 7, in another approach, a hole 77 is dug in the earth. Samples are taken at various horizontally and vertically spaced locations 75 along the generally vertical wall 79 of the hole 77 and, probably, at other locations. The wall 79 and the locations 75 will similarly be mapped with a field sketch.

Irrespective of whether bored or dug holes 69, 77 are used, each such sample location 75 is identified on the sketch with a designator 81 which is unique for that site 67. It is likely that soil samples 11 will be taken from several dozen locations 75 at a particular site 67. For reasons that will become apparent, sampling a site 67 therefore involves having a substantial number of tools 10 available, i.e., at least a quantity equal to the number of locations 75.

Referring now to FIGS. 1 and 6, the designator 81 used for a particular location 75 is that which is marked on the tool 10 used to take that particular sample 11. The designator 81 is preferably prominently marked on the tool 10, e.g., on the barrel. Since a particular tool 10 will be used many times (at different sites 67) and since such tools 10 must be thoroughly washed and cleaned prior to use, marking is preferably permanent by etching, engraving or the like.

Immediately after the sample 11 is taken (and before significant VOC evaporation can occur), the barrel 13 with the possibly-contaminated soil sample 11 inside is then sealed as described above and the tool 10 set aside. The overall length of the tool 10 may be two or three times the length of the barrel 13 alone. Clearly, provision of adequate storage and carrying space for several dozen complete tools 10 becomes a significant concern, especially at a remote field site 67 where working conditions may be less than ideal. In a preferred sampling tool 10, the handle 23 and ejector 29 may be removable from the barrel 13 and plunger 37, respectively. When removed, the aperture 83 is plugged for vapor retention using a plug 85 like that shown in FIG. 4. And, of course, "sample loaded" tools 10 can be stored as is without removing the handle 23 and ejector 29.

Referring to FIG. 8, when all desired samples 11 have been taken, the "sample-loaded" tools 10 are used to place soil samples 11 into vials 53 kept on site 67. Such samples 11 are later analyzed at a laboratory. And each sample 11 is placed into a vial 53 marked with the same designator 81 as is marked on the tool 10 and on the field sketch. The tool 10 thereby becomes the link between a particular location 75 and a particular vial 53 and helps establish a sample "chain of custody".

Sample placement is by uncapping the barrel 13, quickly inserting such barrel 13 into a vial 53 and manipulating the ejector 29 to drive the sample 11 into the vial 53 for virtually-immediate vial capping. In a highly preferred version, the tool barrel 13 has an outside diameter not in excess of, and preferably very slightly less than, about 25 mm. Since many types of appropriately-sized lab vials 53 have a mouth diameter of 25 mm or greater, such a barrel 13 can be readily inserted into such vials and, of course, into vials 53 having larger mouths. As illustrated in FIG. 8, an appropriately-sized barrel 13 closely fits the diameter of the vial mouth 87 to help prevent vapors from escaping.

Figure 11:
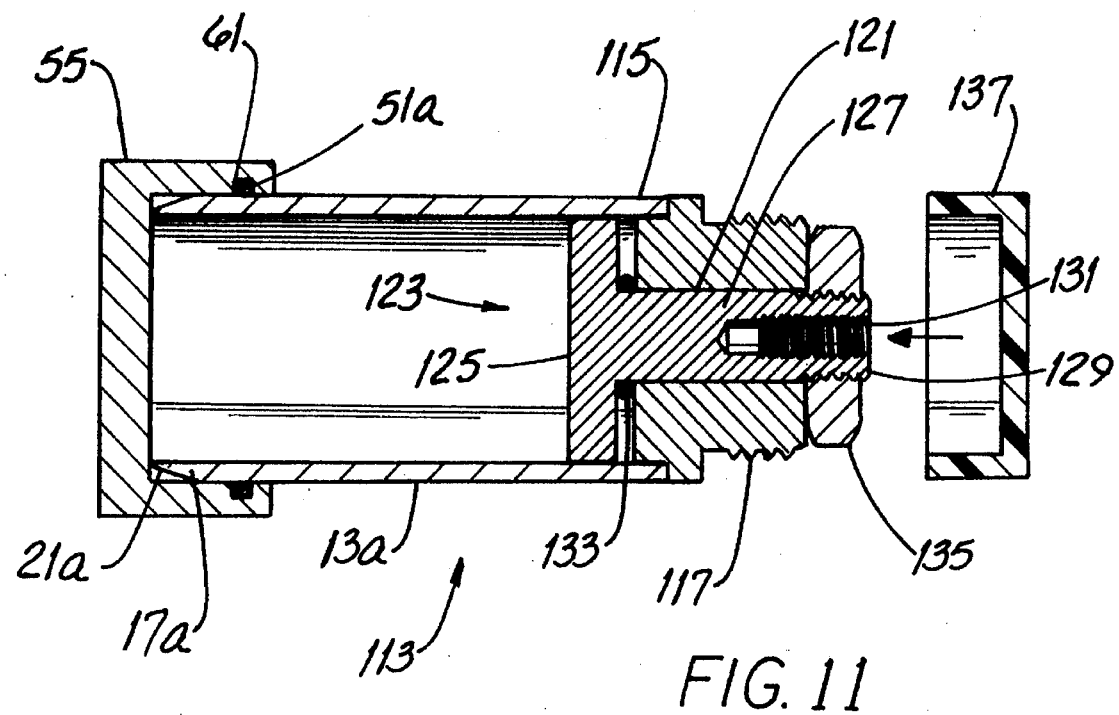
FIG. 11 is a cross-section elevation view of a new sample-preserving cartridge.
Figure 12:
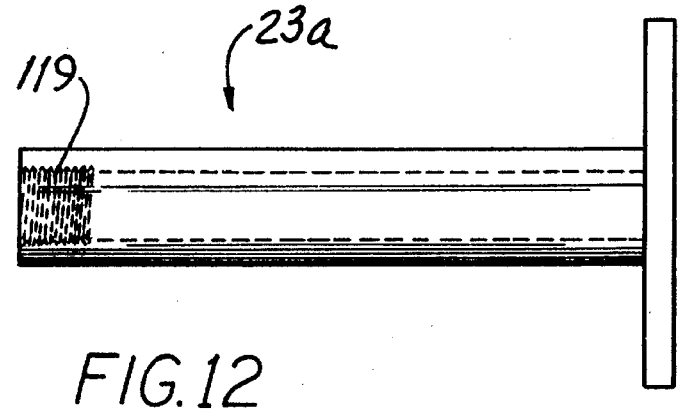
FIG. 12 is a view of a handle used with the cartridge of FIG. 11.

Referring also to FIGS. 11 and 12, another aspect of the invention involves a tool-like cartridge 113 for preserving a core-like soil sample 11 after such sample 11 has been removed from a site 67 possibly contaminated with VOC. A major advantage of the cartridge 113 is that it can be used "on-site" to quickly and completely seal a possibly-contaminated soil sample 11 within such cartridge 113 immediately upon withdrawal of the tool barrel 13a from the soil. Another advantage of such cartridge 113 is that it can be carried "sans handle" for space-saving transportation of the confined soil sample 11 to a laboratory.

The invention has a number of new features configured and arranged to preserve the integrity of a soil sample 11 after it has been extracted and up to actual analysis. The new cartridge 113 has a generally cylindrical barrel 13a with a mouth portion 17a bounded by a relatively thin knife-like edge 21a so that the cartridge 113 may be more easily urged into the earth. At its proximal end 115 opposite the mouth portion 17a, the barrel 13a has an attachment portion 117 to which the threaded end 119 of a handle 23a is attached during actual sample extraction.

The barrel attachment portion 117 and the distal end 119 of the handle 23a are compatibly threaded. The handle 23a can thereby be easily attached to the barrel 13a for sampling and thereafter just as easily detached from such barrel 13a just as easily for transporting the sample.

The structural arrangement that seals the proximal end 115 of the cartridge 113 is as follows. The attachment portion 117 has a "smooth-bore" opening 121 through it and within the barrel 13a is a plug 123 having an imperforate, disc-like face plate 125 and a stud 127 of reduced diameter extending from such plate 125. The end 129 of stud 127 is externally threaded and also has a threaded interior cavity 131. The plug 123 seals an end 115 of the barrel 13a during sample extraction and transport and, as described in more detail below, is later used to expel the soil sample from the cartridge 113.

A sealing member 133 such as a resilient O-ring is interposed between the face plate 125 and the attachment portion 117. After the stud 127 is inserted through the opening 121, a retention device 135 such as a nut is threaded to the stud 127. When the nut is tightened, the O-ring is compressed and the opening 121 is sealed. And there is a cover 137 on the attachment portion 117 as a thread protector when a handle 23a is not attached.

Referring also to FIG. 2, a cap 55 seals the mouth portion 17a. As described above, the cap 55 has an O-ring 51a in a groove 61 and when the cap 55 is in place, the O-ring 51a is compressed and seals against the mouth portion 17a. Like the plug 123, such cap 55 prevents VOC vapors from escaping from the cartridge 113 after sample extraction, while the sample 11 is being transported to a laboratory and until the analyst is ready to remove the cap 55 and expel the sample 11 into a vial for analysis.

Other aspects of the invention involve a method for obtaining a soil sample using the unique tool-like cartridge 113 described above. Such method includes the steps of providing a generally-cylindrical cartridge 113 having an open mouth portion 17a and a proximal end 115 sealed by a removable plug 123.

In preferred practice (and prior to shipment to the customer), the cartridge manufacturer or distributor installs the removable plug 123 by inserting the stud 127 through the opening and tightening the nut. If the prospective user, e.g., an environmental engineering company, has not earlier obtained a suitable handle 23a, such handle 23a is ordered to be supplied with the cartridge 113 or with a group of cartridges 113.

As the user prepares to take a soil sample, the end 119 of the removable handle 23a is attached to the cartridge 113. The cartridge 113 then used to "core out" and extract a soil sample 11.

Immediately following sample extraction, the mouth portion 17a is closed, preferably by applying a cap 55 to such mouth portion 17a. For optimum sealing, the applying step includes compressing the resilient seal 51a between the cap 55 and the mouth portion 17a. And the handle 23a is detached but end closure and handle detachment may be in either order but is preferably done in the order described. Using such method, the soil sample 11 and any VOC therewith is quickly "captured" in the cartridge 113 for preservation, transport and later analysis.

Figure 13:
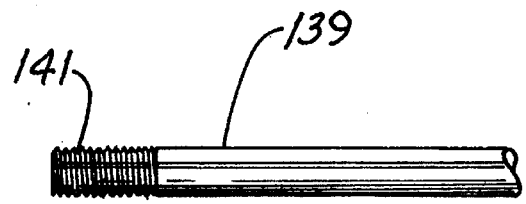
FIG. 13 is a view of a rod-like implement used to urge a soil sample from the cartridge of FIG. 11. Part is broken away.

In other aspects of the method, the handle detaching step is followed by the steps of transporting the cartridge 113 for analysis and, when ready to analyze the sample, moving the plug 123 along the cartridge barrel 13a toward its mouth portion 17a to expel the soil sample from the cartridge 113. To move the plug 123, a rod-like implement 139 (as shown in FIG. 13) is provided for applying force to the plug 123. The implement 139 is coupled to the plug 123 by screwing the implement end 141 into the threaded interior cavity 131 of the plug 123. The plug 123 and soil sample 11 are then pushed out.

It has been found that the new cartridge 113 and the method of its use are major advances in soil VOC analysis since the soil sample need not be removed from the cartridge 113 to be transported. And the integrity of the sample 11 (and any VOC vapors contained therein) is well maintained by the sealing means 51a, 133 at each end of the cartridge 113. That is, VOC vapors are substantially prevented from escaping and contaminants are prevented from entering.

And those are not the only advantages. In practice, users of the cartridge 113 are often repeat purchasers thereof and have obtained a handle 23a with their first cartridge purchase. Similarly, the analyzing laboratory has obtained a rod 139 to urge the plug 123 toward the cartridge mouth portion 17a. Thereafter, it is necessary to supply only cartridges 113 to the user, to ship only soil-containing cartridges 113 to a laboratory and to ship the dirty cartridges 113 back to a cleaning site for cleaning and later re-use. That is, no handle 23a or implement 139 need accompany the cartridge. The aggregate saving in shipping space is very significant.

While the principles of this invention have been described in connection with specific embodiments, it is to be understood clearly that such embodiments are exemplary and not limiting.

What is claimed:

1. A cartridge for preserving a soil sample and including:

a generally-cylindrical barrel having an outer surface and a mouth portion adapted for insertion into soil for collection of a soil sample;

an attachment portion fixed with respect to the barrel and having a single thread-free central opening therethrough;

a plug in the barrel for expelling the soil sample therefrom, the plug including an imperforate face plate in the barrel and a thread-free stud extending axially from the face plate into the opening and closely fitted thereto for sealing such opening; and a cap closing the mouth portion and having a resilient seal against the barrel outer surface, whereby the cartridge is suitable for preserving a substantially-dry soil sample containing a volatile organic compound.

2. The cartridge of claim 1 wherein:

an O-ring sealing member is around the stud and is interposed between the face plate and the attachment portion for sealing the opening.

3. The cartridge of claim 1 including a cover on the attachment portion.

4. The cartridge of claim 2 wherein the cap is manually removable from the barrel without moving the barrel.

5. The cartridge of claim 1 in combination with a soil sample contained therein and wherein:

the stud includes an interior cavity, whereby an implement may be inserted into the cavity for moving the plug and expelling the sample from the cartridge.

6. The cartridge of claim 3 in combination with a handle and wherein:

the attachment portion has exterior threads for handle attachment;

the handle is removably attached to the attachment portion; and the cover protects the threads when the handle is removed.

* * * * *